United States Patent [19]

Mazur

[11] Patent Number: 5,205,824
[45] Date of Patent: Apr. 27, 1993

[54] RETRACTABLE SYRINGE WITH A CLOSED BARREL

[76] Inventor: Matthew S. Mazur, 3366 Columbia St., San Diego, Calif. 92103

[21] Appl. No.: 714,431

[22] Filed: Jun. 13, 1991

[51] Int. Cl.$^5$ ............................................. A61M 5/00
[52] U.S. Cl. ...................................... 604/110; 604/195
[58] Field of Search ............... 604/195, 110, 187, 263, 604/198, 218, 220

[56] References Cited

U.S. PATENT DOCUMENTS

| | | |
|---|---|---|
| 4,026,287 | 5/1977 | Haller . |
| 4,040,421 | 8/1977 | Young ................................... 128/218 |
| 4,159,713 | 7/1979 | Prais ...................................... 128/765 |
| 4,303,070 | 12/1981 | Ichkiawa et al. ..................... 128/218 |
| 4,430,080 | 2/1984 | Pasquini et al. ....................... 604/240 |
| 4,500,310 | 2/1985 | Christinger .......................... 604/228 |
| 4,507,117 | 3/1985 | Vining et al. . |
| 4,592,744 | 6/1986 | Jagger et al. ......................... 604/192 |
| 4,632,672 | 12/1986 | Kvitrud ................................ 604/222 |
| 4,650,468 | 3/1987 | Jennings, Jr. ........................ 604/110 |
| 4,675,005 | 6/1987 | DeLuccia ............................ 604/110 |
| 4,692,156 | 9/1987 | Haller . |
| 4,710,170 | 12/1987 | Haber et al. ......................... 604/195 |
| 4,747,830 | 5/1988 | Gloyer et al. . |
| 4,747,831 | 5/1988 | Kulli ..................................... 604/110 |
| 4,758,232 | 7/1988 | Chak . |
| 4,770,655 | 9/1988 | Haber et al. ......................... 604/110 |
| 4,790,822 | 12/1988 | Haining . |
| 4,790,827 | 12/1988 | Haber et al. ......................... 604/198 |
| 4,808,169 | 2/1989 | Haber et al. . |
| 4,820,272 | 4/1989 | Palmer . |
| 4,824,489 | 5/1989 | Haber et al. ......................... 604/195 |
| 4,838,870 | 6/1989 | Haber et al. ......................... 604/187 |
| 4,883,471 | 11/1989 | Braginetz et al. .................... 604/220 |
| 4,931,040 | 6/1990 | Haber et al. . |
| 4,935,015 | 6/1990 | Hall . |
| 4,950,241 | 8/1990 | Ranford ........................... 604/195 X |
| 4,950,251 | 8/1990 | Haining ................................ 604/195 |
| 4,978,340 | 12/1990 | Terrill et al. ......................... 604/195 |
| 4,986,812 | 1/1991 | Perier . |
| 4,986,813 | 1/1991 | Blake et al. . |
| 4,994,034 | 2/1991 | Botich et al. . |
| 5,030,208 | 7/1991 | Novacek et al. ..................... 604/110 |
| 5,034,002 | 7/1991 | Duranzampa et al. .............. 604/110 |
| 5,047,016 | 9/1991 | Dolgin et al. ........................ 604/195 |

Primary Examiner—John D. Yasko
Attorney, Agent, or Firm—Brown, Martin, Haller & McClain

[57] ABSTRACT

A retractable syringe that pulls the needle and holder from a fluid sealed releasable connection in the open forward end of the syringe barrel to a position enclosed within the barrel, with the piston shaft then being broken off at the piston and the free end of the shaft inserted through the now open forward end of the syringe barrel, enclosing and sealing the needle holder and the remaining fluid in the barrel, with the shaft holding the needle from longitudinal movement within the barrel. The syringe can then be disposed of without allowing access to the needle or having fluid leakage.

42 Claims, 8 Drawing Sheets

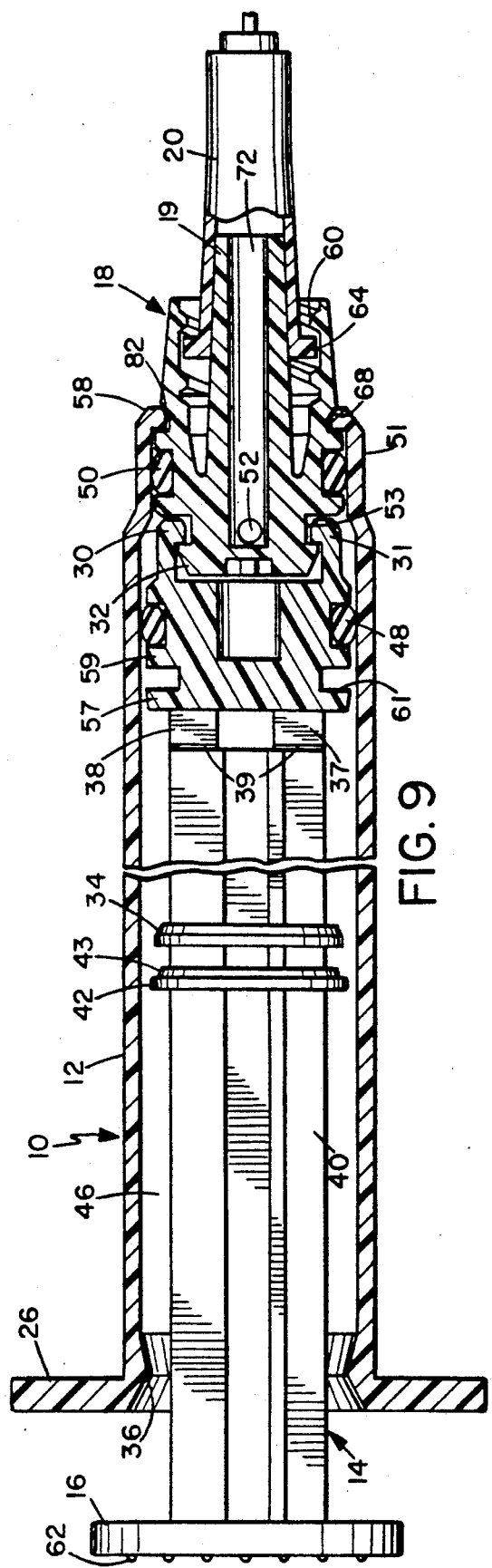
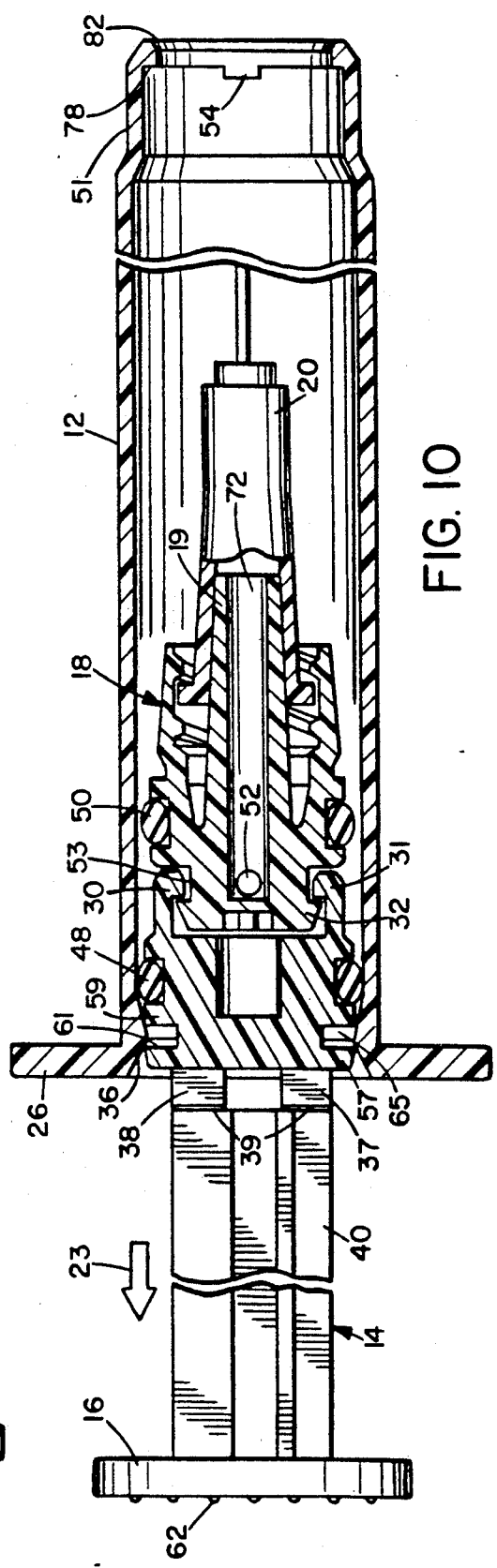
FIG. 9
FIG. 10

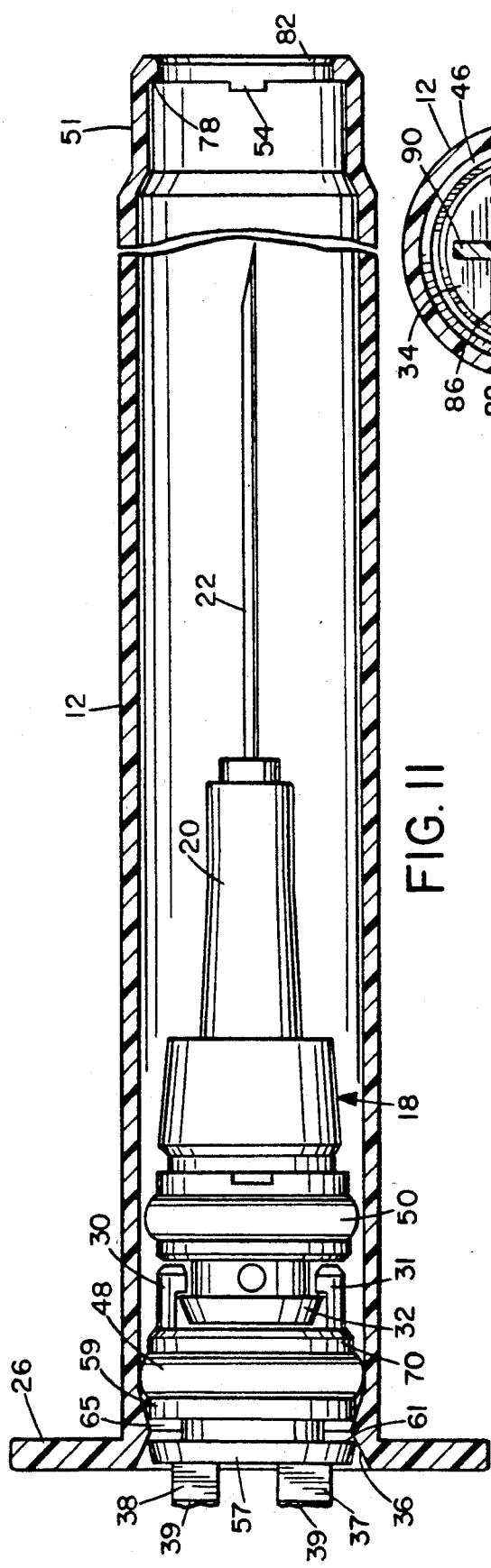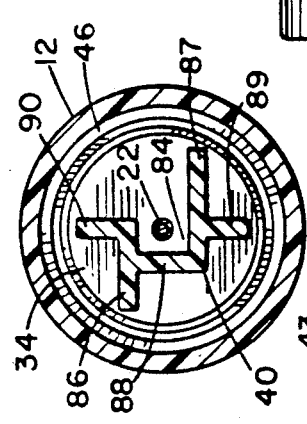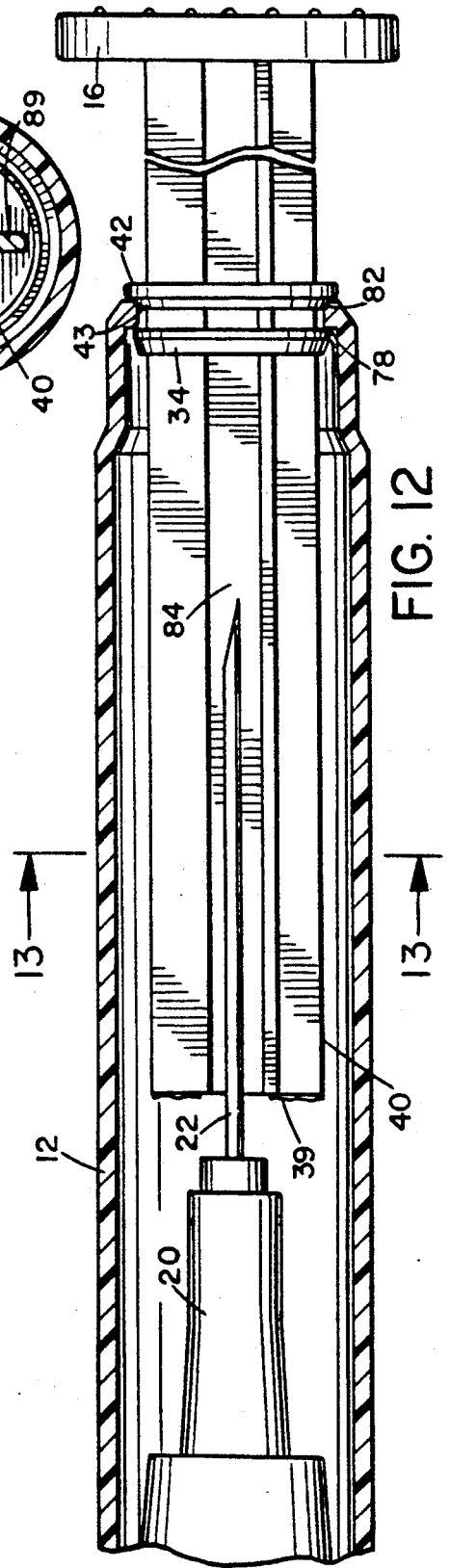

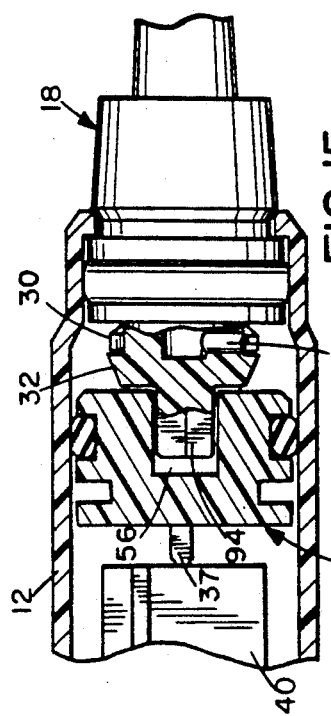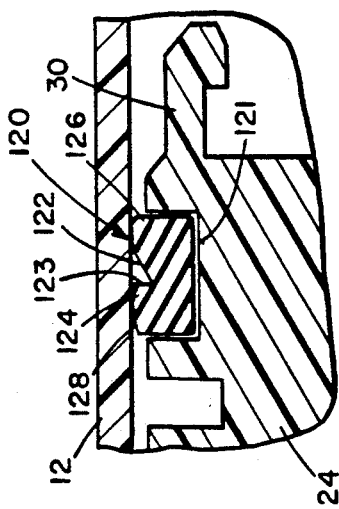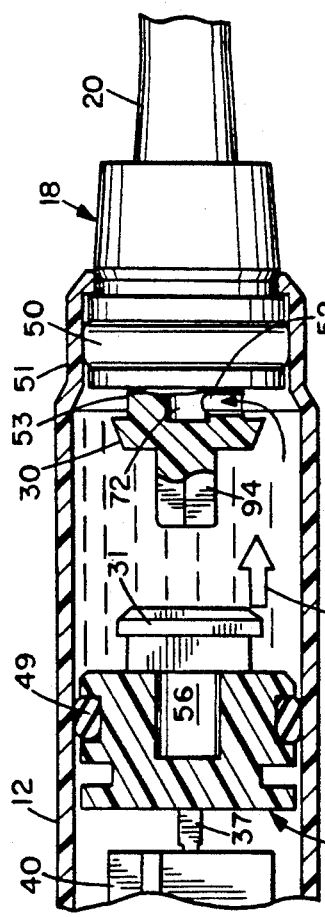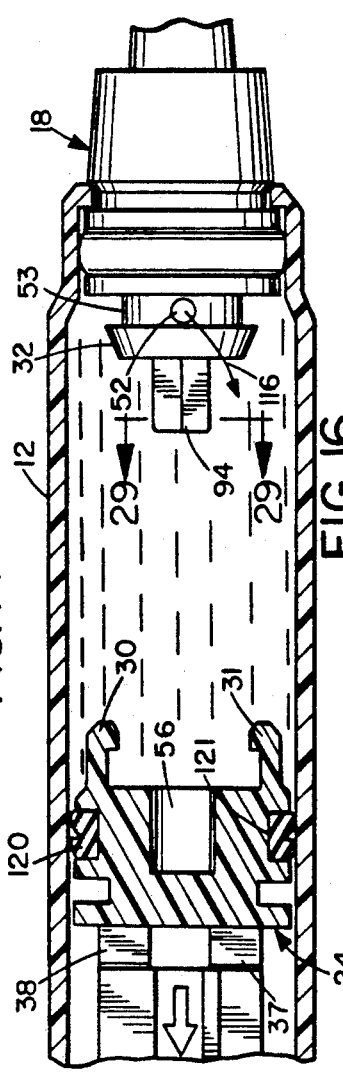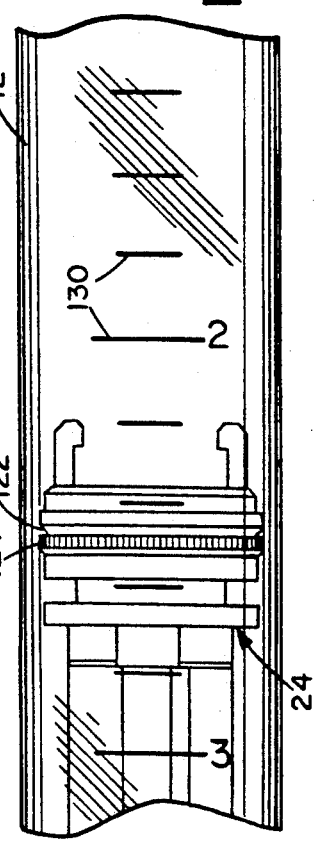

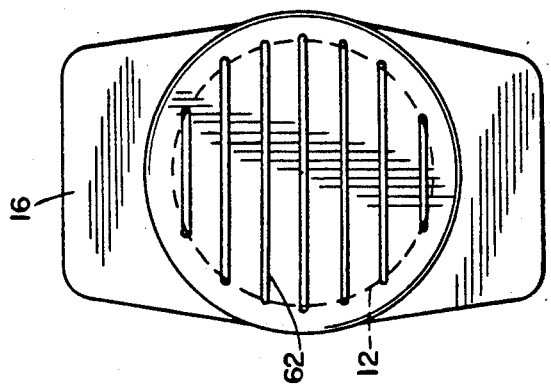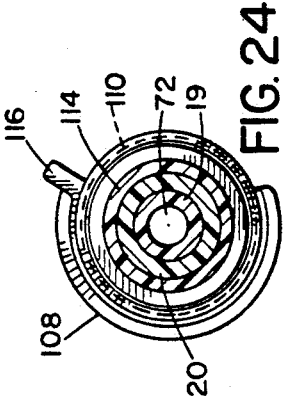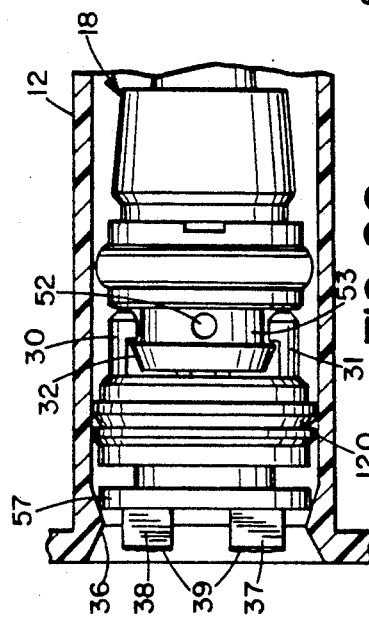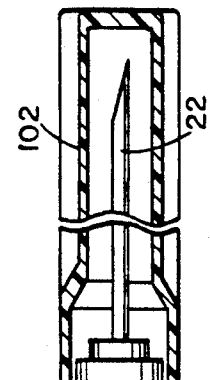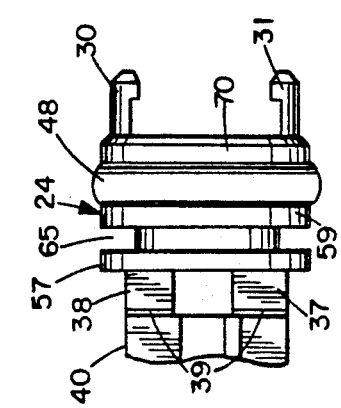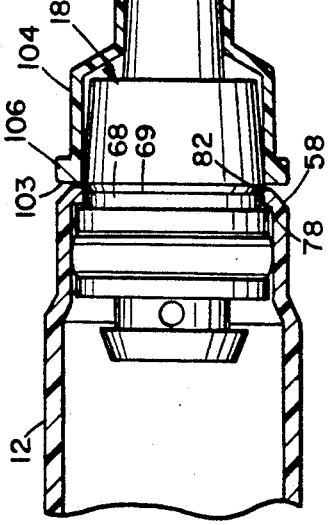

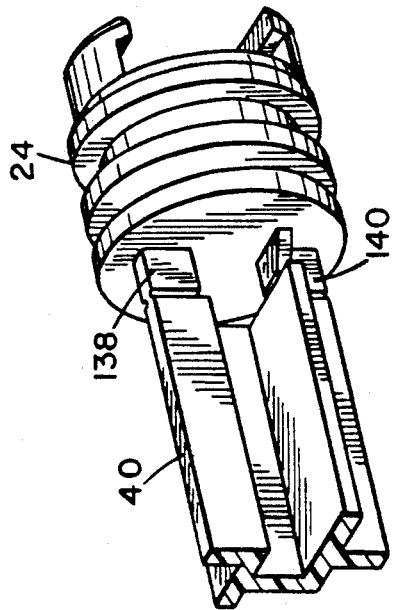
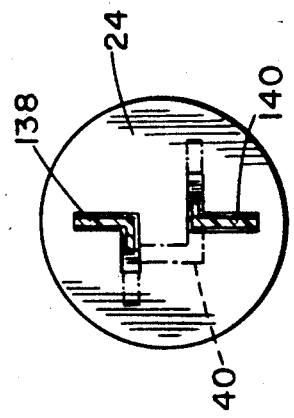
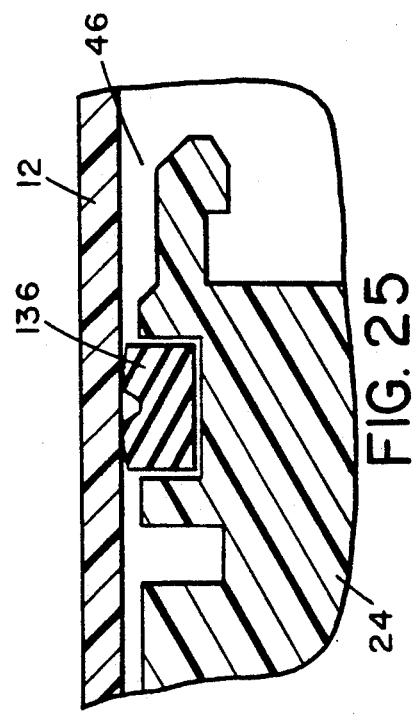
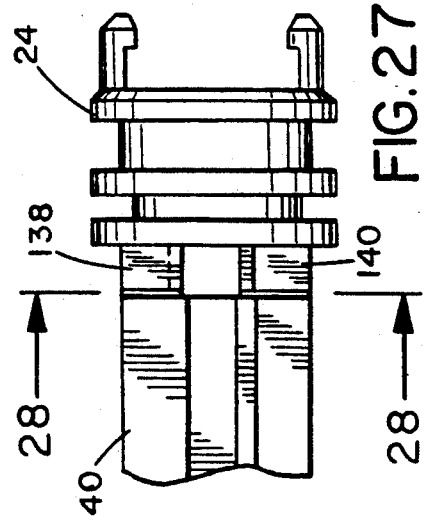

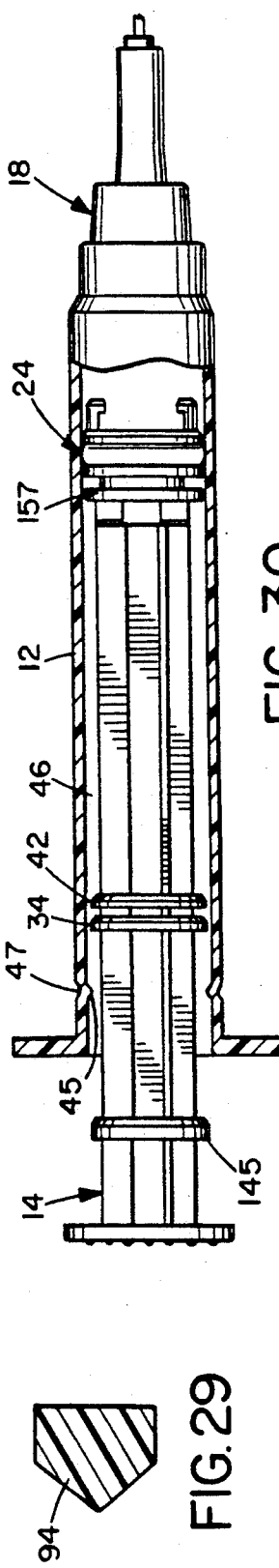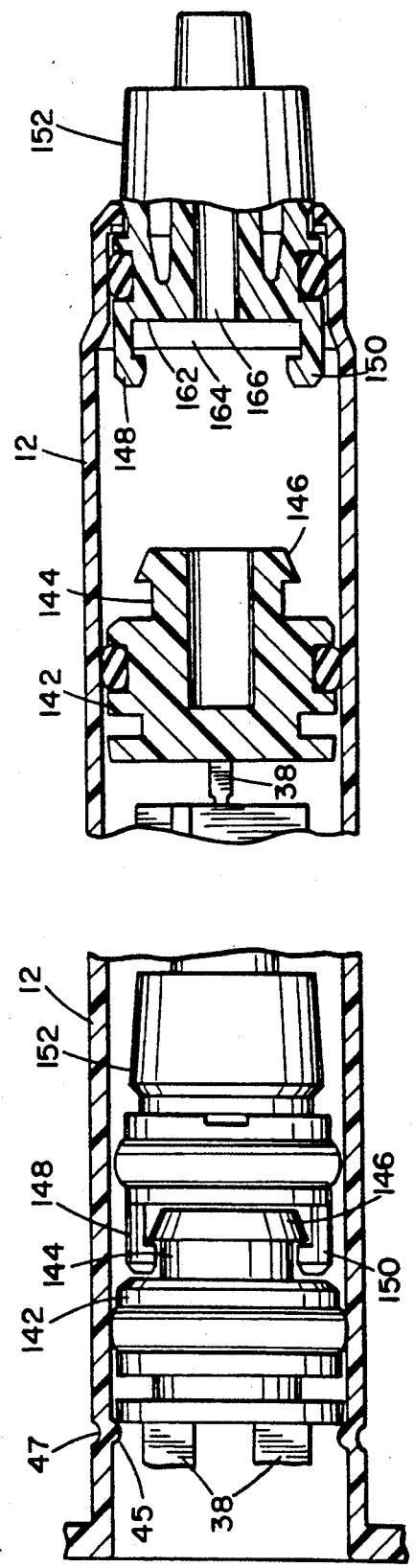

RETRACTABLE SYRINGE WITH A CLOSED BARREL

BACKGROUND OF THE INVENTION

The present day danger to doctors, medics and nurses resulting from using syringes is well known. But to a subsequent user, contagious diseases such as AIDS and hepatitis have made the reuse of a syringe a catastrophic event. Yet notwithstanding all of these dangers and problems, the common syringe that has been sold for years and is still used in volume, remains the same. While this syringe may use a removable sheath, this does not effectively protect against inadvertent needle pricks, that often occur in just trying to return a used hypodermic needle to the sheath. Also sheaths do not protect against the dangerous and highly injurious reuse of hypodermic needles.

There are syringe designs that have the capability of retracting the needle or the needle holder into the syringe barrel, as exemplified in U.S. Pat. Nos. 4,838,870 and 4,650,468 that retract the needle into the barrel, and in U.S. Pat. Nos. 4,747,830 and 4,790,822 that retract the needle holder into the syringe barrel. The latter U.S. Pat. Nos. 4,747,830 and 4,790,822 additionally disclose breaking off the end of the plunger shaft and holding the needle and holder in the barrel.

The approach of retracting the needle or the needle housing into the syringe barrel has theoretical advantages. But in actual use the designs disclosed in the aforesaid patents have proven to be impractical in operation, are not cost effective as they are expensive to manufacture, and present problems in leaving substantial amounts of fluid in the barrel after the needle or needle holder have been retracted. Further the differences in the operation of the new designs relative to the old common syringe are so great that the safety factors achieved are not sufficient to justify their adoption.

The patents disclosing withdrawing the needle into the barrel have very complex mechanisms that have the disadvantage of being costly to make and are basically impractical in operation. The mechanisms within the barrel volume for grasping and retracting the needle are so bulky it is difficult to sufficiently eject the fluid from the syringe barrel. So in retracting, substantial amounts of liquid are left in the barrel to leak out later. Even if this liquid is retained in the barrel, this still leaves the syringe in a less desirable condition for disposal. Essentially a syringe is a very simple device and it has to be kept simple in construction and in operation as well as being inexpensive to make; or it will not achieve wide acceptance because of the large number of syringes that are used each year.

The patents that disclose retracting the entire needle holder and needle into the barrel, likewise have very complex mechanisms for accomplishing the retraction that makes such syringes expensive to make and subject to operation failure. Some of these systems require that the forward end of the syringe be frangible. These syringes all are either not capable of being manufactured at a reasonable cost or cannot be broken easily. Further the frangible section makes the syringe structurally weak at a very critical point, and also makes the syringe unsealable after being broken. Some of these systems also require that the plunger shaft be broken to render the syringe inoperable and to assure that the syringe needle and holder cannot be pushed back out of the forward end of the barrel. The problem with this is that the plunger shafts are difficult to break in practical use. Even if the shaft can be broken, the effort in doing so is distasteful to the syringe user, because the syringe user has to be mindful of the fact that the unattached needle and needle holder can be caused to eject from the syringe barrel and cause an accidental pricking by the hypodermic needle. Further in the systems that retract the needle and holder into the barrel, after such retraction the barrel is essentially not closed at one end. So the fluid is released, making an obvious mess. The two systems design that retract the needle and holder into the barrel have a design that makes the syringe expensive and complex to make, and so the price and complexity makes the syringe design unlikely to be used in the future.

There is therefore, a real and demanding need for a new and improved syringe that easily, quickly and positively retracts the needle and needle holder into a sealed condition within the syringe barrel, which has a means for easily breaking off the shaft from the piston rendering the syringe incapable of future use, and for providing a simple and easy means of sealing the open forward end of the syringe in locked manner so that the syringe needle and holder cannot inadvertently escape or be jarred out of the open end of the syringe barrel, and that provides a new and improved syringe that is relatively inexpensive to make, is simple and positive in operation, that is safe and easy in use, that allows maximum ejection of the fluid from the barrel in use, that locks the needle holder from being inadvertently withdrawn into the barrel, that retains the retracted syringe in the barrel and seals the syringe and the fluids in the barrel, and that can be disposed of in the sealed condition.

SUMMARY OF THE INVENTION

The present invention provides a retractable syringe in which the needle holder is releasably positioned and secured in the forward open end of the syringe barrel. The piston and the shaft operate as a plunger in the syringe, to draw in and dispense liquids in the normal manner. When the syringe has been used and the liquids dispensed, the plunger is forced in with slightly greater force than in normal operation to cause the piston to engage the needle holder. The plunger is then pulled rearwardly pulling the piston and the joined needle holder, releasing the releasable connection to the forward open end of the barrel. The combination piston and needle holder are then retracted to a position adjacent the rear opening of the syringe barrel, where the shaft is broken off at a weakened section adjacent to the piston in a quick and easy manner. The piston retains its position and seals the rear opening of the barrel and restrains the needle holder from movement out the rear end of the barrel. The free end of the shaft is then inserted into the open forward end of the barrel and sealing means attached to the shaft are positioned into the forward open end of the barrel, sealing the barrel and locking the shaft in a position that holds the needle holder from moving around in the barrel.

All of this is accomplished in a simple and straightforward manner, using straightforward and understandable mechanisms, and that does not require major breakage of what are essentially difficult to break components within the syringe structure. The syringe thus ends up with the piston blocking and sealing one end of the barrel, and the shaft sealing and locking the other end of the barrel, with the shaft projecting into contact the needle or needle holder in the barrel, holding the needle from movement. The entire package may then be disposed of in a safe and simple manner.

This does not require the use or reliance upon a sheath to cover the end of the hypodermic needle after it has been used, and does not allow the syringe and needle to be reused, and further restricts any contact with the needle or the fluid that was formerly within the syringe barrel, from being dispensed or spread around in the area of disposal of the used syringe.

It is therefore an object of this invention to provide a new and improved retractable syringe that corrects the shortcomings of other prior retractable syringes.

Other objects and many attended advantages of this invention will become more apparent upon a reading of the following detailed description and an examination of the drawings in which like figures designate like parts throughout and in which:

BRIEF DESCRIPTION OF THE DRAWINGS

FIG. 9 is a view similar to FIG. 5, with the piston latched on the needle carrier;

FIG. 10 is a similar view, with the piston and shaft withdrawn and the needle carrier and needle retracted into the syringe body;

FIG. 11 is a similar view, with the piston shaft broken off and the piston and needle carrier locked in the retracted position;

FIG. 12 is a similar view, with the shaft inserted and locked in the opposite end of the body to enclose the needle;

FIG. 13 is a sectional view taken on line 13—13 of FIG. 12;

FIG. 14 is a view similar to FIG. 5, with a modified alignment means between the piston and the needle holder, and illustrating ejection of fluid;

FIG. 15 is a view similar to FIG. 14, with the piston and needle holder interlocked;

FIG. 16 is a view similar to FIG. 14, with an alternative piston ring and illustrating the drawing of fluid into the syringe;

FIG. 17 is an enlargement of a portion of FIG. 16, with a detail of the piston ring;

FIG. 18 is a side elevation view of the structure of FIG. 16, illustrating the use of the piston ring as a capacity indicator;

FIG. 19 is a side elevation view of a modified form of the piston;

FIG. 20 is a view similar to FIG. 11, showing the piston retained in the syringe with the needle holder attached;

FIG. 21 is an end view of the syringe, illustrating the orientation of the plunger with the syringe body;

FIG. 22 is a side elevation view, partially sectioned, illustrating a pre-use sheath secured over the needle;

FIG. 23 is a similar view illustrating an alternative needle sheath arrangement;

FIG. 24 is a sectional view taken on line 24—24 of FIG. 23;

FIG. 25 is a sectional view similar to FIG. 17, with a different "O" ring;

FIG. 26 is a perspective view similar to FIG. 6 with a different frangible section;

FIG. 27 is a side elevation view similar to FIG. 19 with a different frangible section;

FIG. 28 is a sectional view taken on line 28—28 of FIG. 27;

FIG. 29 is a sectional view taken on line 29—29 of FIG. 16;

FIG. 30 is a side elevation view similar to FIG. 1 with a modified barrel and shaft stabilization construction;

FIG. 31 is a similar view to FIGS. 11 and 31, with the piston and needle holder interconnecting structure being modified in a new embodiment; and FIG. 32 is a side elevation sectional view similar to that of FIG. 5, illustrating the modified embodiment in FIG. 31.

DESCRIPTION OF THE PREFERRED EMBODIMENT(S)

Figure 1:
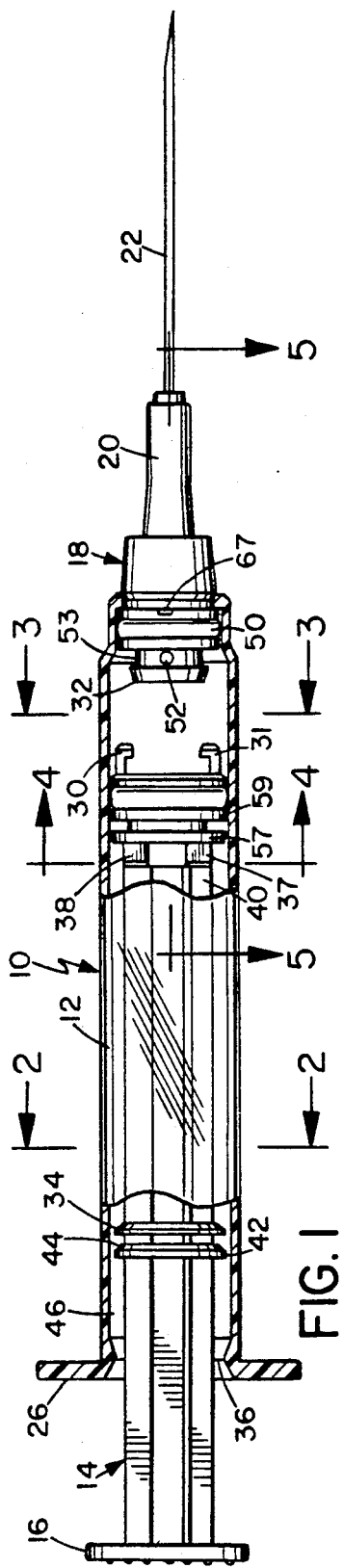
FIG. 1 is a side elevation view of the retractable syringe, with portions cut away.

Referring now to FIG. 1, there is illustrated a retractable syringe 10 having a hollow syringe barrel 12. This barrel and other suitable parts of the syringe are made of a plastic material such as polypropylene. The syringe barrel 12 has a forward end 15 and a rearward open end 17. Releasably positioned in the forward end is the needle holder assembly 18. A movable plunger has a piston 24 with an O-ring seal that is connected to a shaft 14 that extends out the open end 17 of the barrel 12. A thumb driven actuator surface 16 at the end of the shaft 14 coacts with finger grip 26 on the open end of the barrel 17 to push and pull the piston 24 in the barrel in the manner of operating the syringe. The piston 24 has means or grasping the end 32 of the needle holder 18, which will be described in more detail hereinafter, and pulls the needle holder rearwardly to the point that the needle holder 18, the needle housing 20 and the needle 22 are all moved into a retracted position within the syringe barrel as illustrated in FIG. 11. With the needle holder in this position, the needle 22 is entirely enclosed within the volume of the barrel 12. The shaft 14 is then broken off from the piston 24, and the free broken end of the shaft 14 is then inserted through the forward open end 15 of the barrel 12. The shaft thus functions to close off the open forward end of the barrel with the piston closing off the rearward open end of the barrel, securing and enclosing the retracted needle within the barrel. Both ends of the barrel are thus closed and are sealed by the piston at one end and the shaft at the other end, so that the needle and the remaining fluid are both sealed within the barrel. The barrel is now ready for disposal.

In other embodiments, the piston and joined needle holder can be locked in the barrel, or are prevented from being pulled out the rear open end of the barrel. A separate "C" clip lock means prevents the needle holder from being moved from the releasable connection until released by the syringe user. Also the space between the barrel and the needle holder is sealed by an "O" ring seal.

In still another embodiment, see FIGS. 31 and 32, the rear end of the needle holder 152 has the grasping means, fingers 148 and 150. The adjacent forward end of the piston 142 has a projection with a circumferential slot 144. The fingers grip the end of the piston 142, and locks the piston and the needle holder together. Then pulling the plunger rearwardly pulls the piston 142 and the secured needle holder 152, from the open end of the syringe to the retracted position as previously described.

Referring now to FIGS. 1, 5, 6 and 9, the piston 24 has an outer circumferential groove 49 for receiving an O-ring 48. O-ring 48 may be made of any suitable material and functions as a movable seal between the piston and the inner surface of the barrel 12. The "O" ring is preferably made of rubber. It has been discovered that rubber functions as a better seal against the plastic barrel, than plastic against plastic. The groove 49 has sufficient width and depth to prevent the O-ring 48 from rolling over or out of groove 49. Thus the O-ring 48 functions as a wiper for wiping inner surfaces of the barrel along with moving the fluid by virtue of the piston action both into and out of the hollow syringe barrel 12. The piston 24 has an axially centered recess 56 that receives and co-acts, in one embodiment of the syringe, with a nut type alignment 94, see FIGS. 14, 15 and 16, as will be described in more detail hereinafter. The front end of the piston 24 has a pair of arcuate members 30 and 31 each of which form fingers with internal shoulders 33 that co-act to slide over the rear cam surface 27 on the rear end of the needle holder 18. The fingers 30 and 31, see FIG. 3, have sufficient resilient biasing to cause the fingers to be cammed outwardly by the cam surface 27 to snap in, fit in or grip into the groove 32 of the needle holder 18. However, the fingers 30 and 31 are only arcuate sections, and do not enclose the entire circumference of groove 32, for reasons that will be explained in more detail hereinafter.

Figure 4:
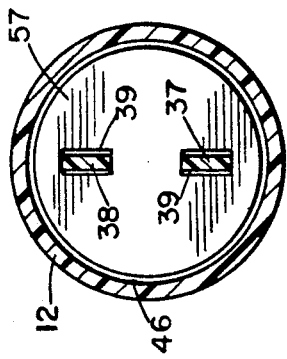
FIG. 4 is an enlarged sectional view taken on line 4—4 of FIG. 1.

The piston also has a circumferential slot 65 between a pair of rims 57 and 59, that have an outer diameter slightly smaller than the inner diameter of the barrel. These rims 57 and 59 provide longitudinal stability to movement of the piston and also for other functions that will be described hereinafter. The piston 24 is connected to a piston shaft 14 by a pair of radially spaced frangible members 37 and 38, see FIGS. 4 and 5, that in turn are connected to a plurality of interconnected lath type members that are formed into a substantially outer rectangular configuration that corresponds with the inner surface of the barrel. The composite interconnected lath type members forms a circumferential cross sectional area, see FIG. 2, with each of the lath members being connected along their longitudinal adjacent edges. Lath member 90 is connected to the side edge of lath member 86 that is in turn connected to lath member 88 that is connected to lath member 87 that has a side projecting lath member 89. It may be understood that this entire composition shaft structure 40 provides lateral rigidity against bending force moving the piston 24. This configuration provides an open center space in the syringe barrel 12 for receiving the end of the needle and needle housing 20 when the shaft 24 is inserted into the open end of the barrel 15 as illustrated in FIG. 12. Collars or discs 34 and 42 are molded into the shaft 14 and extend outwardly, see FIGS. 1 and 2, to provide centralized positioning of the shaft in the barrel 12.

Figure 2:
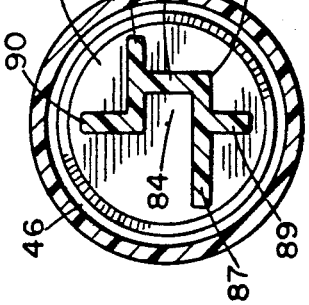
FIG. 2 is an enlarged sectional view taken on line 2—2 of FIG. 1.

The frangible sections comprise lath type members 37 and 38, see FIGS. 1, 4, 5 and 6, that are radially aligned and have a relatively thin cross-section. These lath members may be broken when subjected to lateral bending forces in a given direction. These lateral bending forces are resisted by the other cross sectional configuration of the lath member 14 as previously described and as illustrated in FIG. 2. The lath members 37 and 38 are also scored at 39 on either side or both sides of each member, which further facilitates the breaking of the frangible sections 37 and 38. The frangible members interconnect the remainder of the shaft with the rear side of the piston 24, thus allowing shaft 24 to be broken at a point adjacent to the piston.

In another embodiment, see FIGS. 26, 27 and 28, a modified frangible section is substituted for the lath members 37 and 38, primarily to provide added lateral stability. In this embodiment the lath members 138 and 140 corresponding respectively to lath members 37 and 38, and are made with an "L" shaped cross-section. The bottom of the "L" shape for each section is integral with the adjoining lath members 86 and 87. Each of the "L" shaped members are scored at 139 and 141 on all sides except the outer edges 151, to facilitate breakage of the shaft in the manner previously described.

The rear open end 17 of the barrel 12 has a V-shaped inner surface 37 that narrows the diameter of the opening. The respective collars 34 and 42 have a smaller diameter than the inner diameter of ring surface 36, and thus pass freely therethrough. However, the piston 24 has larger diameter rims 57 and 59 that restrain the piston from movement out of the open end 17 and through the inward V-shaped ring surface 36. In one embodiment, see FIGS. 9 and 10, the diameter of rim 57 is slightly larger than the inner diameter of ring surface 36 and rim 57 has an angled, canted outer edge surface that allows rim 57 to contact and be cammed through the V-shaped ring 36. Thus the inward V-shaped projection 36 snaps into the slot 65. The outer diameter and shape of piston rim 59 is relatively square and thus the outer side edges of rim 59 contact the side surfaces of the V-shaped projection 36 and prevents passage through opening 17. This effectively locks the piston into the open end 17 of the rear portion of the barrel 12.

Thus a pulling force on end plate 16 pulls the plunger, and thus the shaft 14 through the open end 17, and also pulls the piston. The end rim 57 will contact the side of the V-shape projection 36. With a slight increase in force, rim member 57 can be pulled through opening 17 camming the canted surface of member 57 through the opening of the inner surface of the V-shaped ring 36. This causes the V-shaped ring to be secured in the manner previously described, and thus locks and holds piston 24 in the opening 36. The resilient pressure of the outer edges of the slot 65 against the sides of the inner ring surface 36 is sufficient to provide a fluid seal against fluid movement out of the open end 17. Further, O-ring 48 also functions to prevent outward fluid movement from the barrel 12 through open end 17.

It may be understood that the piston 24 may be initially inserted into the barrel 12 by pushing the piston through the restricted neck 36 in the open end 17 of the barrel. This is accomplished by exerting considerable longitudinal force on the piston by the shaft 24. This force is sufficient to move the piston and the outer rim portions 57 and 59 through the neck 36. However, when the neck 36 is snapped into the slot 65, this essentially locks the piston in the secured and sealed position where it is held against the normal application of forces against the piston that would occur in normal operation of the syringe. While the force required to move the piston from this locked position, as for example that force required to insert the piston through the neck 39 in initial installation, would normally not occur in the operation of the syringe.

In another embodiment, see FIGS. 19 and 20, the piston has a different shaped rim member 92 that does not have the canted outer end surface and also has an outside diameter generally corresponding to the diameter of rim 59. So in rearward movement of the piston, the outer edge surface of rim 92 contacts the side of the inner shape ring 36, see FIG. 20, in the manner that prevents movement of the ring 92 of the piston out of the open end 17 and through the inner ring-shaped projection 36. Accordingly, ring projection 36 does not snap into slot 65, and the piston is not locked into the open rear end of the barrel in this embodiment. Rather, the piston is pulled to the end of the open end of the barrel, and it remains in that position. It may be understood that when the shaft 14 is broken off, O-ring 88 exerts sufficient outward pressure against the inner surface of the syringe barrel 12 to hold the piston 24 against longitudinal movement within the barrel, and to provide a seal against fluid movement.

The needle 22 is held by a needle housing 20 in the known manner. The needle holder 18 has an internal threaded recess in its forward end for receiving the standard end 64 of a needle housing 20. The needle housing 20 is threaded into the threads 60 and is held in position. The wide space between the thread bights in threads 60 allows the needle holder 18 to hold or interconnected different, standard needle housing designs. Needle holder 18 has a conical forward outer end surface with a first circumferential groove 68. Groove 68 has a forward canted cam surface 82 and a rear abutment section 28 that forms one side of an O-ring recess for holding O-ring 50 in position. The forward open end 15 of the barrel has a reduced diameter end 51 that terminates into a neck with a lip 58 that has an internal circular hook portion 78 that fits into the groove 82 in the needle holder. The outer internal edge of the lip 58 has an outwardly canted rim surface that coacts with the cam surface 82 to provide a releasable latch for holding needle holder 18 in position. It may be understood that in inserting the holder 18 into the open end 15 of the barrel 12, the canted surface on the forward end of the holder 18 contacts the inner surface of the lip 58 and cams through the opening to the latched position. The material from which the barrel is made is slightly flexible with a resilient memory that returns the flexed lips 58 to the original position. This causes lips 58 to snap into the slot 82, locking the surface of the ring slot 28 and retaining the needle holder against longitudinal movement in the open end 15 of the barrel 12. When the needle holder 18 is pulled rearwardly into the barrel 12 as will be described hereinafter, the cammed surfaces of lip 58 are cammed by the canted surface of recess 82, allowing the needle holder 18 to be pulled through the opening 15 and into the barrel 12. The O-ring 50 provides a fluid seal in opening end 15. Again, preferably the O-ring is made of rubber. Also, the O-ring seal maintains a fluid seal around the needle holder end during slight rearward movements of the needle holder.

The needle holder 18 has an axially positioned fluid passage 72 that connects to the fluid passage of the needle housing 20 and needle 22. Channel 72 is connected to a radial channel or passage 52 that conducts fluid into and out of the volume of barrel 12. When the piston 24 is pulled in the direction of arrow 118 a vacuum is drawn by the piston in the chamber volume 46. This draws fluid through the needle 22, passage 72, passage 52 into the volume 46 and fills the syringe barrel with fluid. In the fluid ejection or injection mode, the end 16 of the shaft 14 is pushed toward the finger hold 26 causing the shaft 14 to move the piston head 24 in the direction of arrow 96, see FIG. 4, which causes the fluid to flow out through radial passage 52 and through passage 72 and out the end of needle 22. At the end of the discharge stroke, the longitudinal pressure on the shaft may be increased and continued causing the fingers 31 to cam over the end surface 32 of the rear end of the needle holder 18, and thus hook or grasp into the circumferential slot 32. The fingers 30 in grasping the needle holder 18, secures the needle holder to the piston 24. So when the piston 24 is pulled rearwardly, the piston pulls the needle holder with it, causing the needle holder to cam open the lips 58 of the open end 15 of the barrel. This pulls the needle holder 20 and needle 22 into the enclosed position as illustrated in FIG. 11.

The increased force required to cause the fingers of the piston to grasp the needle holder is of such magnitude that the syringe user has to intentionally and thus knowingly increase the force. So accidentally joining the piston to the needle holder doesn't normally occur.

In operation of the syringe it is desirable to be able to view the fluid in the barrel, and particularly the forward end of the barrel volume 46. The barrel in this invention is transparent, so this volume may be observed by looking through the side of the barrel and particularly at the passageway 52, to determine whether there is air or fluid in the forward end of the barrel, or whether the air has been bled out of the barrel. So in removing air bubbles from the barrel 10, the needle is directed upwardly and the piston 24 is moved to cause fluid to pass through the needle 22 thus ejecting the air. In this operation it is necessary that the volume around passage 52 be observable to assure that no air has collected in the end of the barrel. So it's also necessary that the grasping fingers 30 and 31 are aligned as in FIG. 1, so as not to block viewing the volume 48 and passageway 52. Accordingly in initial construction of the syringe, the plunger i.e. the piston is aligned through rotating the thumb pressing member 16, which aligns the fingers 30 and 31 in the groove so that they do not shield the opening of passage 52. Only a single passageway 52 is shown to conduct fluid from volume 48 to passageway 72. It may be understood that there may be more than one of such passageways through the end of the needle holder, but the preferred embodiment has only a single passageway as it has been found that a single passageway is better capable of conducting fluid and air from volume 48 out through passageway 72, and not trapping or retaining an air bubble in the upper end of the volume 48, in operation of the syringe.

In other embodiments of the invention, see FIGS. 31 and 32, the barrel 12 has a straight inner cylindrical surface without the inward V projection 36 of FIG. 1. In this embodiment, the barrel is dimpled 47 by a dimple tool to provide an inward projection 45. It may be understood that the material from which the barrel 12 is made is of a very tough, durable, and yet slightly ductile, resilient material. Accordingly a known dimple machine may strike the side of the barrel 12, impacting the side of the barrel and causing a dent or dimple 47 that results in an inward projection or dimple projection 45. Thus, see FIG. 31, the outer configuration of the rear ring member 157 of the piston 24, which has the configuration as illustrated in FIG. 20 as ring 57, moves into an abutting contact with the inward projection 45, preventing the piston from being withdrawn from the barrel 12 without exerting a very large and intentional forces that would be obvious to the user. This dimpling functions to prevent the piston from being pulled out of the barrel 12 in normal operation. Also in this embodiment, the discs 34 and 42 have a diameter slightly less than the distance between the dimples, and accordingly the two discs 34 and 42 pass through the opening between the inner projections 45. This also applies to the ring or disc member 45. Ring or disc member 45 is a second collar or disc member that it secured to the shaft at a location closer to the end of the shaft, and which ring 45 functions to provide added stability against lateral movement by the shaft in its longitudinal movement in the volume 46 of the barrel 42.

In another feature of the invention, the needle holder 18 has a slot 67 in circumferential groove 68 that receives the key 54 that is molded into the lips 58 of the barrel 12, see FIGS. 1, 11 and 20. When assembled, the key 54 is fitted into key slot 67 by positioning means 92 or 94, that rotate the needle holder relative to the barrel. This locks the needle holder in position and prevents rotation of the needle holder 18 when screwing the end of the needle housing into the internal threaded recess 64. This also allows alignment of the passageway hole 52 with the barrel 12 so that the finger grip 26 can be aligned with the bars 62 on the thumb presser 16 to correctly orient the fingers 30 and 31 with the needle holder 18 and the passageway 52.

In inserting the holder 18 into the open end of the forward end 15 of the barrel 12, a tool such as a male key driver fits into and coacts with the shape of recess 92 in the rear end of the needle holder 18. This aids in moving the forward end of the needle holder through the lips 58 and also allows needle holder 18 to be rotated to the point that key 54 fits into slot 67 of the needle holder 18.

In another embodiment, a nut-shaped end 94, see FIGS. 14 and 15, projects outwardly from the rear end of needle holder 18. A suitable wrench then fits over nut 94 and is rotated thereby, which aids in pushing the needle holder 18 into position and also to rotate and orient slot 67 with the key 54. Further, end 54 substantially fills the volume 56 in the end of piston 24, reducing the amount of fluid left in volume 46 of the barrel 12 after the fluid has been ejected through the needle 22, and also after the piston has been latched to the needle holder to pull the needle holder and needle into the barrel 12. In pulling the needle holder and needle into the barrel 12, it is desirable to eject as much fluid as possible from the syringe volume.

In still another embodiment, the O-ring 48 in piston 24 comprises a split O-ring, see FIGS. 16 and 17. The O-ring slot 121, which preferably is made of O-ring rubber, is larger than the radial slot 49 in FIG. 4 and the O-ring 120 has a wider, rectangular cross-sectional shape. The outer circumferential surface of O-ring 126 has a groove 122. This groove provides a pair of outer contacting surfaces 124 and 126 that provide a separate spaced wiping surface combination for wiping and sealing fluid moved by piston 24. A slanted edge surface 128 on one end, aids in restricting roll-up of the rearward edge of the O-ring 120, when pulling a vacuum in volume 46. Further, the circumferential aperture 122 has a defined edge 123 that co-acts with calibrated metering lines 130 on the barrel 12 to allow measurement of fluid in the barrel 12. In a modified embodiment, see FIG. 25, the O-ring 136 is substituted for O-ring 120 on piston 24. O-ring 136 provides the same operational advantages as O-ring 126 and is symmetrical, simplifying installation.

It may be understood that the side edges of the O-ring 120 as well as O-ring 48 are such that it restricts rolling movement of the O-ring 48 with movement of the piston 24. The advantage of the split O-ring 120 in FIGS. 16 and 17 is that it further restricts such rolling movement, and also provides a double seal along with providing a relatively visible line on which to calibrate the fluid in the barrel relative to the position of piston 24. Also the wider contact surface of the split O-ring 126 provides a wider contact surface with the barrel. This increases the holding force on the piston when the piston is in the retracted position and after the shaft has been broken, and the piston is not locked into the open end 17 of the barrel. Further this wider and larger surface contact also holds the piston against side movement and thus creates a longer force holding the needle against dropping by gravity when the piston and needle are retracted in the barrel and the shaft has been broken.

Referring to FIGS. 1 and 12, when the shaft has been broken, and the free end has been inserted into the open forward end 15 of the barrel 12, the two collars or disc members 34 and 42 are thus caused to lock the shaft into the neck or lips 58 of the open barrel end. The disc 34, has a solid construction, see FIG. 2, and has a canted surface. This canted surface when contacting lips 58, allows the disc 34 to pass through the opening. This then places the lips 58 in a locked position in space 44, and provides a sealing surface contact with the sides of discs 34 and 42. Further, since both discs are solid a double seal occurs between disc 34 and disc 42.

Also encompassed within the inventor's invention is a needle cover or syringe cover 100. This cover has a closed end 102 with an open end 103 having an internal configuration for fitting over and against the conical outer surface of the needle holder 18, and has a radial end surface at ring shoulder 106 that abuts against the forward surface of the lip 58 of the barrel 12. If an impact occurs against the end of the needle cover or sheath 100, this force is transmitted directly against the forward end of the barrel 12 and does not exert a rearward force against the needle holder 18, that could otherwise cause the needle holder to be released by the lip 58.

In another embodiment, a third groove 110 is provided in the end of the needle holder, see FIGS. 23 and 24. This groove 110 receives a snap, half ring or C-clip 108 that is shaped to fit into the groove 110 and be retained in the position by its circular configuration that is slightly larger in circumference than one-half of the circumference of the groove. The snap ring has an open section that allows the ring to be inserted laterally into groove 110. In this position, the needle housing 118 is restrained from any rearward movement that would cause the housing 118 to cam through the lip latching means 58 at the end 17 of the barrel 12. This allows a standard needle sheath 114 to be mounted onto the needle holder 120. The retention clip 112 has an outward projecting nob 116 that is usually pushed circumferentially by the thumb of a user, which snaps the snap ring 112 out of groove 110. This releases the needle housing to be pulled by the piston into the barrel of the syringe.

In operation of the syringe with a C-clip, the syringe user normally first expels air from the syringe by pushing the piston forward in the barrel. In this operation, an error could occur where the syringe user pushed the barrel too far and with too much force, causing the piston and needle holder to become engaged. With the C-clip in place, the user can just exert even greater force in pulling the piston rearward, and with the needle holder held by the locking C-clip, the fingers cam outwardly allowing the piston to disengage from the needle holder, returning the syringe to its original condition, where it is ready for use.

Further in normal operation of the syringe, the user usually inserts the syringe and makes the injection. After the injection has been made, and the syringe user pushes the plunger in with the syringe user's right thumb, the syringe user normally grasps the side of the barrel with their left hand, steadying the syringe as it is pulled from the person who received the injected fluid. When the syringe and needle is withdrawn from making the injection, then the syringe user can just push the plunger forward with force sufficient to engage the plunger and the needle holder. With the user's left hand on the barrel, the user merely moves their thumb forward and in flipping the thumb against the nob, flips the C-clip out of the slot or groove. Thus the needle holder is now released from the C-clip lock, and may be pulled wit rearward force on the piston, to the retracted position in the barrel.

IN OPERATION

In assembly, the barrel 12 and the syringe 10 receives the needle housing 18 through the opening in the rear end 17 of the barrel 12. Any suitable tool pushes the needle housing 18 through the lip 58, which causes the lip to be resiliently biased into the outer groove of the housing 18, thus releasably holding the housing 18 in position. A suitable wrench which may also be the driver for inserting the housing 18 into the barrel and into position, is used to rotate the housing 18 to the correct orientation as set by the key 54 and the slot 68. The shaft 14 and piston 24 are then rotated by the finger pressure end 16 to correct alignment with the finger actuating flanges 26, to align the hole passage 52 with fingers 30 and 31.

The shaft 14 thus drives the piston 48 into the cylinder 12 to a location immediately adjacent the rear end 27 of the housing 18. The syringe piston 24 is then moved to draw fluid through the needle 22 into the volume 46 of the barrel 12. After the fluid is drawn into the barrel volume 46, the plunger is then pushed forward by the finger thumb pressure end 16 and shaft 14, with fluid being exited through the needle 22, to remove air from the piston volume 46. The fluid then flows through passage 52 to the inner passage 72 and out the needle 22. Fluid is then injected in the normal operation of the syringe with the piston 24 moving the measured amount as determined by the calibration units on the barrel, see FIG. 18. When the desired fluid has been ejected through the needle 22, then any remaining fluid is further ejected by movement of the piston 24 into contact with the end 32 of the needle housing 18, with the fingers 30 and 31 engaging the end of the needle housing 18. In this latched integral condition, the plunger 24 is then pulled by pulling on the shaft 14, in the rearward direction. This force is sufficient to cause the lips 58 to be cammed out of the slot 68, thus releasing the needle housing 18 to be pulled through the opening in end 15 to the internal retained position where the needle is totally enclosed within the barrel 12.

In one embodiment, the piston is pulled into contact with the end of the restricted diameter of the rear end of the barrel 12, see FIG. 11, or in the embodiment in FIG. 10, greater force is exerted onto the shaft 14 and piston 24, pulling it into the locked position of Figure 10. In either position, the weakened portions 37 and 38 of the shaft member 14 are at the end opening of the syringe barrel 12. The shaft 14 is then bent laterally breaking the shaft connection to the piston 24, thus breaking members 37 and 38 which may be along the score lines 39. The shaft 14 is then free from the piston 24, and is inserted into the now open end 17 of the barrel 12, see FIG. 12. The shaft is inserted directly into the barrel with the needle 22 being positioned in the center space of the composite shaft structure, see FIG. 13. The slanted radial end of the collar 54 cams through the lip opening 58. The lip 58 is then secured in slot 44, as the outer diameter of collar 42 is greater than that of collar 34. This locks the shaft 14 into the open end of the barrel 12. Since the collars 34 and 42 are solid, a fluid seal also is created by the contact between collars 34 and 42 with the lip 58. It may be understood, that in this position the needle 22 may by virtue of gravity have a tendency to not hold its central position. However, the central space 84 in the shaft 14 is open to one side, allowing the needle to fit into the space 84, regardless of its position. It may be understood that the O-ring 48, see FIG. 11, also seals the other end of the barrel 12, thus holding the needle 22 in a fluid sealed barrel 12 and being restrained from movement longitudinally at both ends of the barrel 12. In this condition, the entire unit is then disposed of, rendering the syringe incapable of further use, and also prevents the needle from contact or inadvertently penetrating or pricking the skin of the person using the syringe. Thus the person using the syringe is protected against inadvertent happenings with the syringe, and also allows the syringe to be disposed of in a manner that prevents fluid loss, other similar messes, and also in a manner that renders the syringe incapable of reuse.

As further protection, the needle is provided with a sheath that is positionable over the needle and the needle holder and housing, and will absorb any type of impact force on the end of the syringe, without causing the needle holder to be released and moved into the internal volume of the syringe. In another embodiment, an additional lock clip is used to also prevent inadvertent forces being applied to the syringe that would cause the syringe holder to be inadvertently moved longitudinally into the barrel of the syringe. In one embodiment, the holder is removed from the syringe, and the syringe is immediately used in the manner previously described. In the second embodiment, a standard syringe sheath is removed from the end of the syringe, allowing the syringe to be used in the normal manner. Then before retraction, the lock clip is removed from the forward end of the syringe, and the syringe is then retracted in the manner previously described.

Figure 3:
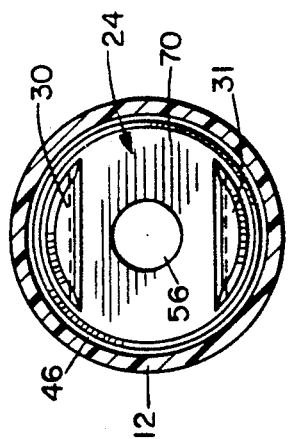
FIG. 3 is an enlarge sectional view taken on line 3—3 of FIG. 1.
Figure 5:
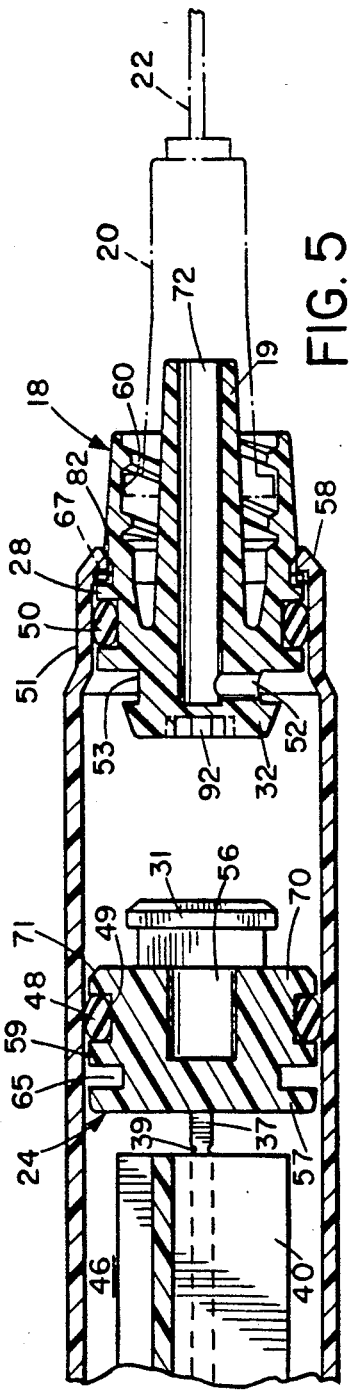
FIG. 5 is an enlarged sectional view taken on line 5—5 of FIG. 1.
Figure 7:
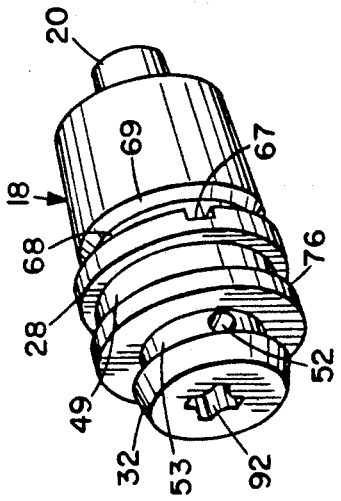
FIG. 7 is a perspective view of the needle carrier.
Figure 6:
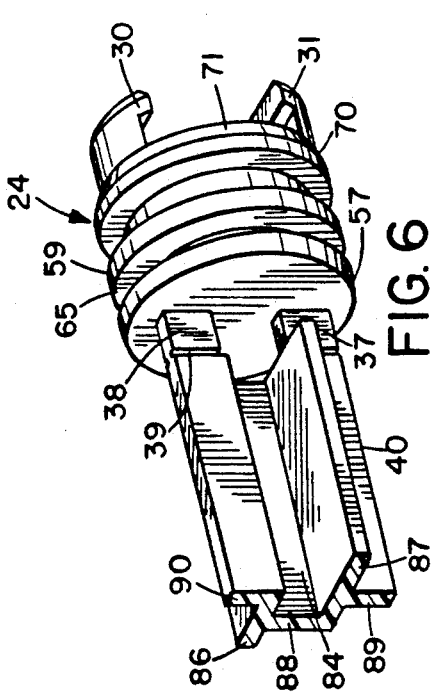
FIG. 6 is a perspective view of the piston end of the plunger.
Figure 8:
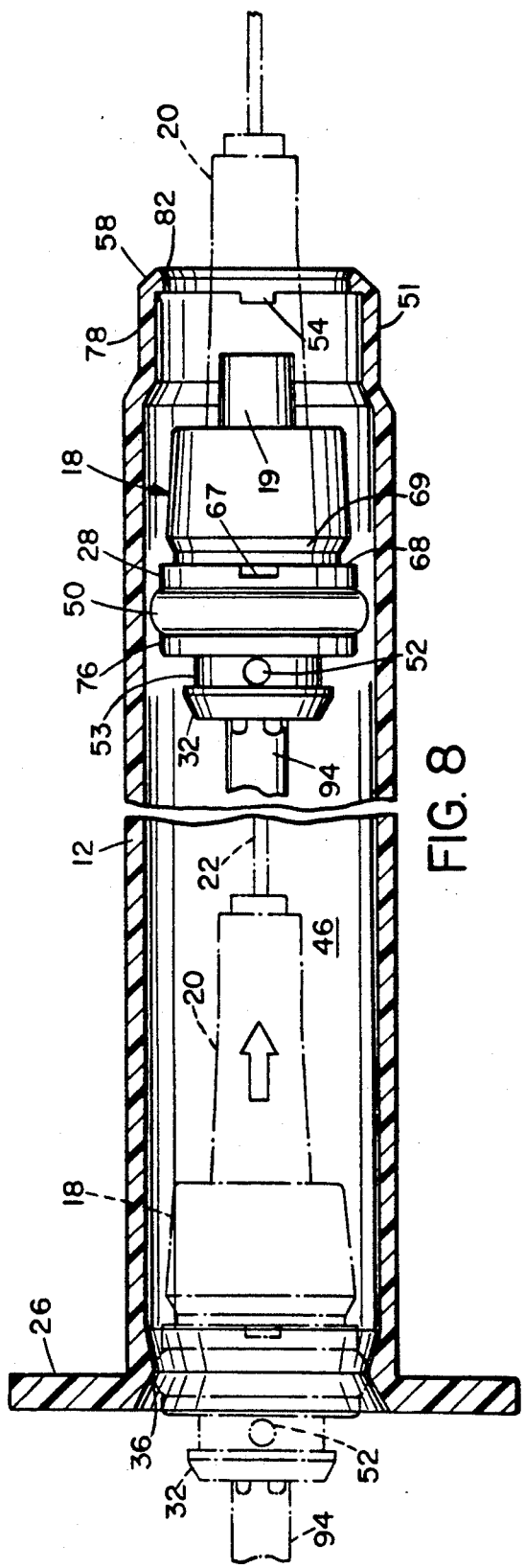
FIG. 8 is a longitudinal sectional view of the syringe body, illustrating the initial insertion of the needle carrier.

In another embodiment, see FIGS. 31 and 32, piston 24 and needle holder 18 as previously illustrated in FIGS. 1 and 5, are modified to new piston 142 and new needle holder 152. The new piston 142 does not have the grasping fingers, but instead has a projection having an outer frusto-conical end 146 with an inner forward outer circumferential slot 144. This end projection cooperates with the respective fingers 148 and 150 on the rearward end of the needle holder 152, that correspond with the fingers 30 and 31 previously described relative to FIG. 1. The fingers have the same shape as illustrated in FIG. 3, and are cammed outwardly by the frustoconical surface 146 to spring the fingers 148 and 150 apart so that the ends of the fingers pass into the slot 144, securing the piston 142 to the needle holder 152. Force is then exerted onto the piston 142 to pull the piston 142 rearwardly. This in turn pulls the needle holder 152 in the manner previously described, to the retracted position. The inner rearward surface 162 of the needle holder 152 provides a cavity for Collection of the fluid in the syringe, which fluid passes out through opening 166 to the needle 22. The inward canted surface 164 on the inner surface of the barrel 12, functions to help position the needle holder 152 when inserting the needle holder 152 into the retained position, and also to direct the fluid towards the flat surface 162 and thus into a central passageway 166.

When the C clip 108 is in position, the needle holder cannot be moved rearwardly into the barrel, either inadvertently or intentionally. For example, in operation of the syringe the user may force the piston by pressing on end 116 with sufficient force that it causes the fingers 30 or 31 to pass into the rear slot 53 and then secure the piston and needle holder together. This could render the syringe inoperable, other than to pull the needle holder out of the end of the barrel and secure the entire syringe into the inoperable condition as previously described. However, with the C clip in position, the operator merely exerts a larger pulling force on end member 16, pulling the plunger sufficiently to cause the fingers 30 and 31 to release their grip on the groove 52, separating the piston from the needle holder. This returns the syringe to its starting condition. The increased force required to engage the piston with the needle holder is sufficient that in normal operation the user would recognize that the piston was being forced into a locking position with the needle holder. Yet even if this were to occur, the piston and the needle holder can still be separated by exerting sufficient force to pull the fingers out of the groove 52. The fingers can be pulled out of groove 52 and the fingers are constructed of a plastic that is tough and yet has a degree of flexible resilience that allows the fingers to be cammed outwardly to release the needle holder and locking connection with the fingers 30 and 31 of the piston 24. Regardless of the force exerted on the plunger to pull the plunger from connection with the needle holder, the force will not be sufficient to overcome the locking abutment of the C clip. This same operation occurs relative to the embodiments illustrated in FIGS. 31 and 32, where fingers 148 and 150 will be pulled out of the slot 160 of the projection 144.

Having described my invention, I now claim:

1. A retractable syringe, comprising:
   a syringe barrel with open forward and rearward ends and a piston and shaft in the barrel with one end of the shaft extending out the rearward open end, said shaft having a pair of spaced collars along its length for locking the shaft in the inserted position in the rearward end of the barrel, the rearward end of said barrel having a lip at the open end with a diameter slightly smaller than the diameter of the collars, said lip moving over one of said collars to be locked between the collars;
   a needle holder and needle fitting into the forward end of the barrel in a releasable connection that releases the needle holder for movement toward the rearward end and to a retracted position where the barrel encloses the needle holder and needle, and the forward end of the barrel is open;
   said piston and needle holder having engaging means for securing the piston to the needle holder;
   said piston being movable in said barrel for pulling the needle holder out of said releasable connection to the retracted position; and
   said shaft being breakable along its length with the broken end of the shaft inserted into the forward end of the barrel holding the needle holder and needle in the retracted position.

2. A retractable syringe as claimed in claim 1 wherein,
   said one of said collars having a canted outer circular rim surface for camming said first collar through the lip at the rearward end of the barrel.

3. A retractable syringe as claimed in claim 2 wherein,
   said collars on said shaft have an outer circular dimension that is slightly smaller than the internal diameter of said barrel providing lateral stability of said shaft in movement in said barrel.

4. A retractable syringe as claimed in claim 1 wherein,
   means adjacent the rearward opening and on said piston that locks the piston and the grasped needle holder in the retracted position.

5. A retractable syringe comprising:
   a syringe barrel with open forward and rearward ends and a piston and shaft in the barrel with one end of the shaft extending out the rearward open end, said shaft having a portion along its length that is comprised of a pair of aligned lath members spaced across the diameter of the cross section of said shaft, with the inner edge surfaces being spaced from the cross sectional center of said shaft, whereby said shaft may be broken by moving the rear end of said shaft in a direction normal to the alignment of said two members;
   a needle holder and needle fitting into the forward end of the barrel in a releasable connection that releases the needle holder for movement toward the rearward end and to a retracted position where the barrel encloses the needle holder and needle, and the forward end of the barrel is open;
   said piston and needle holder having engaging means for securing the piston to the needle holder;
   said piston being movable in said barrel for pulling the needle holder out of said releasable connection to the retracted position, with the broken end of the shaft inserted into the forward end of the barrel holding the needle holder and needle in the retracted position.

6. A retractable syringe as claimed in claim 5 wherein,
   said weakened section being adjacent to said piston.

7. A retractable syringe as claimed in claim 5 wherein,
   said pair of radially aligned lath section interconnecting the front end of said shaft with the rear surface of said piston.

8. A retractable syringe as claimed in claim 5 wherein,
   said pair of lath members being scored on the sides thereof.

9. A retractable syringe as claimed in claim 5 wherein,
said barrel has adjacent said rearward opening an inward projecting member,
and said piston has an outer surface for abutting against said inward member, blocking movement of said piston out the open end of said barrel.

10. A retractable syringe as claimed in claim 9 wherein,
said inward projecting member comprising spaced dimples.

11. A retractable syringe as claimed in claim 10 wherein,
said dimples having a given diameter therebetween,
and said shaft having an outer rim adjacent the rearward end of the shaft with a diameter slightly smaller than said given diameter for laterally stabilizing said shaft in movement of said barrel.

12. A retractable syringe as claimed in claim 5 wherein,
a sheath having a closed forward end and rear open end that fits over the forward end of the needle holder and needle,
the rear open end has a shoulder that abuts the forward end of said barrel, whereby when said sheath is positioned over said needle and needle holder, forces applied to said sheath are exerted against the end of the barrel.

13. A retractable syringe as claimed in claim 5 wherein,
said needle holder has a forward groove,
an arcuate lock clip for fitting into said groove and abutting the front end surface of said barrel,
whereby said lock clip positioned in said groove, prevents rearward movement of said needle holder.

14. A retractable syringe as claimed in claim 13 wherein,
said lock clip having a "C" shape with a slightly larger circumference than half the circumference of said groove for being laterally snapped in said slot and being resiliently retained in position,
and one end of said clip has a projection that may be actuated to remove said lock clip from said slot.

15. A retractable syringe as claimed in claim 5 wherein,
said piston having a circumferential slot at its forward end,
and the needle holder having fingers at its rearward end with inwardly directed ends for fitting into said slot, securing the needle holder to said piston.

16. A retractable syringe as claimed in claim 15 wherein,
the forward end of said piston has a frusto-conical collar adjacent said slot,
and said fingers comprising said radial sections that are cammable over said frusto-conical surface into latching engagement between the needle holder and the piston.

17. A retractable syringe as claimed in claim 16 wherein,
said needle holder has an internal fluid passage that communicates with said needle.

18. A retractable syringe as claimed in claim 5 wherein,
said shaft having a weakened section along its length for breaking said shaft.

19. A retractable syringe comprising:
a syringe barrel with open forward and rearward ends and a piston and shaft in the barrel with one end of the shaft extending out the rearward open end, said shaft comprising a plurality of longitudinal members joined at adjacent surfaces to provide a composite cross-section that extends in two dimensions, increasing lateral stability of the shaft;
a needle holder and needle fitting into the forward end of the barrel in a releasable connection that releases the needle holder for movement toward the rearward end and to a retracted position where the barrel encloses the needle holder and needle, and the forward end of the barrel is open;
said piston and needle holder having engaging means for securing the piston to the needle holder;
said piston being movable in said barrel for pulling the needle holder out of said releasable connection to the retracted position; and
said shaft being breakable along its length with the broken end of the shaft inserted into the forward end of the barrel holding the needle holder and needle in the retracted position.

20. A retractable syringe as claimed in claim 19 wherein,
said members comprising laths joined together in a cross-sectional configuration with an outer radial diameter slightly less than the inner radial diameter of the barrel.

21. A retractable syringe as claimed in claim 20 wherein,
said lath members are arranged in a cross sectional configuration that when in the barrel, the center space of said barrel is longitudinally open, for receiving the needle and needle holder when the broken end of said shaft is inserted into the open end of said barrel.

22. A retractable syringe comprising:
a syringe barrel with open forward and rearward ends and a piston and shaft in the barrel with one end of the shaft extending out the rearward open end, said piston having an outer rectangular shaped circumferential slot with an O-ring having a substantially rectangular cross-section and a rearward edge surface canted radially inward, said O-ring positioned in said slot fitting against the inner surface of said barrel for forming a movable seal;
a needle holder and needle fitting into the forward end of the barrel in a releasable connection that releases the needle holder for movement toward the rearward end and to a retracted position where the barrel encloses the needle holder and needle, and the forward end of the barrel is open;
said piston and needle holder having engaging means for securing the piston to the needle holder;
said piston being movable in said barrel for pulling the needle holder out of said releasable connection to the retracted position; and
said shaft being breakable along its length with the broken end of the shaft inserted into the forward end of the barrel holding the needle holder and needle in the retracted position.

23. A retractable syringe as claimed in claim 22 wherein,
said O-ring positioned in the outer radial slot of said piston having a split outer radial surface with a radially inward space in said outer surface, providing a pair of separate outer resilient circumferential contacts between the O-ring and the inner surface of said barrel.

24. A retractable syringe comprising:
a syringe barrel with open forward and rearward ends and a piston and shaft in the barrel with one end of the shaft extending out the rearward open end;
a needle holder and needle fitting into the forward end of the barrel in a releasable connection that releases the needle holder for movement toward the rearward end and to a retracted position where the barrel encloses the needle holder and needle, said needle holder having a rearward circumferential slot, the forward end of said piston having fingers, each said finger having an inward projection for fitting into said circumferential slot for securing said piston to said needle holder, said needle holder having an internal fluid passageway communicating with said needle, said fluid passageway having an end on said circumferential slot;
a second passageway comprising a single chamber with an opening in said slot;
the ends of said fingers having arcuate surfaces for providing open spaces in said slot;
said shaft having indication means for orienting said arcuate surfaces on said fingers to expose and not cover said passageway;
said piston being movable in said barrel for pulling the needle holder out of said releasable connection to the retracted position; and
said shaft being breakable along its length with the broken end of the shaft inserted into the forward end of the barrel holding the needle holder and needle in the retracted position.

25. A retractable syringe as claimed in claim 24 wherein,
said rearward end of said needle holder has a frusto-conical collar adjacent said slot,
and said fingers comprising radial sections that are cammable over said frusto-conical surface into latching engagement between the piston and said needle holder.

26. A retractable syringe as claimed in claim 24 wherein,
said slot and said inward projection having coacting camming surfaces to release for rearward movement of said needle holder.

27. A retractable syringe as claimed in claim 24 wherein,
said inward projection and said needle holder slot having an interacting key and slot that locks the needle holder against rotating movement in the forward end of the barrel.

28. A retractable syringe as claimed in claim 27 wherein,
the rear surface of said needle holder has an internal recess for being accessed by a tool that rotatably positions said holder in the opening of said barrel.

29. A retractable syringe as claimed in claim 27 wherein,
the rear surface of said needle holder has a radially centered nut surface for coacting with a wrench to rotatably orient said needle holder in the open forward end of said barrel.

30. A retractable syringe comprising:
a syringe barrel with open forward and rearward ends and a piston and shaft in the barrel with one end of the shaft extending out the rearward open end, the forward end of said piston having fingers with inwardly directed ends,
a needle holder and needle fitting into the forward end of the barrel in a resiliently contractible connection that resiliently holds the needle holder from movement toward the rearward end to a position where the barrel encloses the needle holder and needle,
said piston having a grasping device that pulls the needle holder out of said resiliently contractible connection to the enclosed position in the barrel,
said needle holder has an outer slot, a second circumferential slot rearward of said outer slot, an O-ring positioned in said second slot for radially sealing the inner barrel opening adjacent the forward end, and a third rearward circumferential slot for engaging said fingers therein,
and the forward end of said barrel has an inward, resilient, circumferential lip that resiliently fits into said outer slot, resiliently holding the needle holder in the forward end of the barrel.

31. A retractable syringe as claimed in claim 30 wherein,
the rearward end of said needle holder has a frusto-conical surface adjacent said third slot,
and said fingers comprising radial sections that are cammable over frusto-conical surface into latching engagement between the piston and said needle holder.

32. A retractable syringe as claimed in claim 31 wherein,
said lip and said slot having a radially directed key slot and key that locks the needle holder against rotating movement in the forward end of the barrel.

33. A retractable syringe as claimed in claim 32 wherein,
the rear surface of said needle holder has means for engaging a tool that rotatably positions said needle holder in the opening of said barrel, engaging said key in said key slot.

34. A retractable syringe comprising:
a syringe barrel with open forward and rearward ends and a piston and shaft in the barrel with one end of the shaft extending out the rearward open end, said shaft having an outer ring portion midway its length with a diameter slightly smaller than the inner diameter of said barrel, for stabilizing said shaft in movement in said barrel,
a needle holder and needle fitting into the forward end of the barrel in a resiliently contractible connection that resiliently holds the needle holder from movement toward the rearward end to a position where the barrel encloses the needle holder and needle,
said needle having a grasping device that grasps the end of the piston,
the piston being movable in said barrel for pulling the needle holder out of said resilient contractible connection to an enclosed position within the barrel, and
said rear opening in said barrel having inward projections for restricting pulling said plunger and piston out of said barrel.

35. A retractable syringe as claimed in claim 34 wherein,
said needle holder has a forward groove, an arcuate lock clip having a C-shape for fitting into said groove and abutting the front end surface of said barrel, whereby said lock clip positioned in said groove, prevents rearward movement of said needle holder.

36. A retractable syringe as claimed in claim 34 wherein, a sheath having a closed forward end and a rear open end that fits over the forward end of the needle holder and needle, and the rear open end has a shoulder that abuts the forward end of said barrel, whereby when said sheath is positioned over said needle and needle holder, forces applied to the sheath are exerted against the end of the barrel.

37. A retractable syringe comprising:

a syringe barrel with open forward and rearward ends and a piston and shaft in the barrel with one end of the shaft extending out the rearward open end;

a needle holder and needle fitting into the forward end of the barrel in a releasable connection that releases the needle holder for movement toward the rearward end and to a retracted position where the barrel encloses the needle holder and needle, and the forward end of the barrel is open;

said piston and needle holder having engaging means for securing the piston to the needle holder;

said piston being movable in said barrel for pulling the needle holder out of said releasable connection to the retracted position;

said shaft being breakable along its length with the broken end of the shaft inserted into the forward end of the barrel holding the needle holder and needle in the retracted position;

said piston having a circumferential slot, and said rearward open end of said barrel having an V-shaped inward ring that fits into said circumferential slot, retaining said piston in a locked retractable position in said open end;

said circumferential slot in said piston having a pair of adjacent outer side edges that fit against each side of the inward ring providing a fluid seal therebetween.

38. A retractable syringe comprising:

a syringe barrel with open forward and rearward ends and a piston and shaft in the barrel with one end of the shaft extending out the rearward open end, said piston having a circumferential slot, and said rearward open end of said barrel having an inward projection;

and the radial outer surface of the rearward end of said piston having a larger diameter than the inner diameter of the projection in the rear open end of said barrel, for preventing said inner rim surface from fitting into the rear radial slot;

a needle holder and needle fitting into the forward end of the barrel in a releasable connection that releases the needle holder for movement toward the rearward end and to a retracted position where the barrel encloses the needle holder and needle, and the forward end of the barrel is open;

said piston and needle holder having engaging means for securing the piston to the needle holder;

said piston being movable in said barrel for pulling the needle holder out of said releasable connection to the retracted position; and said shaft being breakable along its length with the broken end of the shaft inserted into the forward end of the barrel holding the needle holder and needle in the retracted position.

39. A retractable syringe comprising:

a syringe barrel with open forward and rearward ends and a piston and shaft in the barrel with one end of the shaft extending out the rearward open end;

a needle holder and needle fitting into the forward end of the barrel in a releasable connection that releases the needle holder for movement toward the rearward end and to a retracted position where the barrel encloses the needle holder and needle, and the forward end of the barrel is open, said needle holder having a first circumferential slot;

said forward opening of said barrel having a circumferential lip, said lip fitting in said slot for releasably securing said needle holder in a releasable position;

said needle holder having a second circumferential slot rearward of said first circumferential slot, and an O-ring positioned in said slot for resiliently sealing the inner barrel opening adjacent the forward end, said piston and needle holder having engaging means for securing the piston to the needle holder;

said piston being movable in said barrel for pulling the needle holder out of said releasable connection to the retracted position; and said shaft being breakable along its length with the broken end of the shaft inserted into the forward end of the barrel holding the needle holder and needle in the retracted position.

40. A retractable syringe comprising:

a syringe barrel with open forward and rearward ends and a piston and shaft in the barrel with one end of the shaft extending out the rearward open end, said forward end of said syringe barrel having inward projections;

a needle holder and needle, said needle holder having a slot, said inward projections of said syringe barrel fitting into said slot in a releasable connection that releases the needle holder for movement toward the rearward end and to a retracted position where the barrel encloses the needle holder and needle, and the forward end of the barrel is open;

said piston and needle holder having engaging means for securing the piston to the needle holder;

said piston being movable in said barrel for pulling the needle holder out of said releasable connection to the retracted position; and said shaft being breakable along its length with the broken end of the shaft inserted into the forward end of the barrel holding the needle holder and needle in the retracted position.

41. A retractable syringe comprising:

a syringe barrel with open forward and rearward ends and a piston and shaft in the barrel with one end of the shaft extending out the rearward open end, said piston having an outer circumferential slot with an O-ring positioned in said slot fitting against the inner surface of said barrel for forming a movable seal, said barrel having metering marks along the length thereof that coact with one of the edge surfaces of said outer radial space of said O-ring for providing metering indication of fluid in said barrel;

a needle holder and needle fitting into the forward end of the barrel in a releasable connection that releases the needle holder for movement toward the rearward end and to a retracted position where the barrel encloses the needle holder and needle, and the forward end of the barrel is open;

said piston and needle holder having engaging means for securing the piston to the needle holder;

said piston being movable in said barrel for pulling the needle holder out of said releasable connection to the retracted position; and said shaft being breakable along its length with the broken end of the shaft inserted into the forward end of the barrel holding the needle holder and needle in the retracted position.

42. A retractable syringe comprising:

a syringe barrel with open forward and rearward ends and a piston and shaft in the barrel with one end of the shaft extending out the rearward open end, a needle holder and needle fitting into the forward end of the barrel in a connection that resiliently holds the needle holder from movement toward the rearward end to a position where the barrel encloses the needle holder and needle, said piston and needle holder having engaging means that interconnects the piston and the needle holder, whereby pulling the piston towards said rearward end pulls the needle holder out of said resiliently contractible connection to the enclosed barrel, said piston has an outer circular slot with an O-ring positioned in said slot, said O-ring having a split outer radial surface with at least a pair of spaced wiping surfaces separated by an inward space therebetween, and said O-ring fitting against the inner surface of said barrel forming a movable seal.

* * * * *